United States Patent [19]

Boyer

[11] 4,168,206

[45] Sep. 18, 1979

[54] IMPREGNATED DISK METHOD FOR TESTING ANTIFUNGAL SUSCEPTIBILITY

[75] Inventor: Jere M. Boyer, Havertown, Pa.

[73] Assignee: Philadelphia College of Osteopathic Medicine, Philadelphia, Pa.

[21] Appl. No.: 792,619

[22] Filed: May 2, 1977

[51] Int. Cl.$^2$ ............................................. C12K 1/04
[52] U.S. Cl. ..................................................... 435/32
[58] Field of Search ................. 195/103.5 K, 103.5 M

[56] References Cited

U.S. PATENT DOCUMENTS

| | | | |
|---|---|---|---|
| 2,904,474 | 9/1959 | Forg | 195/139 |
| 3,107,204 | 10/1963 | Brown et al. | 195/103.5 K |
| 3,713,985 | 1/1973 | Astle | 195/103.5 M |

OTHER PUBLICATIONS

Shadomy et al., Manual of Clinical Microbiology, 2nd. Ed., pp. 569-574 (1974).

*Primary Examiner*—Alvin E. Tanenholtz
*Attorney, Agent, or Firm*—Seidel, Gonda, Goldhammer & Panitch

[57] ABSTRACT

A method for testing the susceptibility of fungi to antifungal agents comprises inoculating a non-nutrient material, such as agar, with a fungus. A number of disks impregnated with various types and concentrations of antifungal agents and the proper nutrient medium for the type of fungus and antifungal agent tested is placed upon the non-nutrient medium inoculated with fungus. After an incubation period, the plates are read to determine the minimum inhibitory concentration of the particular antifungal agent for the particular fungus. The minimum fungicidal concentration can also be determined upon further incubation.

15 Claims, No Drawings

IMPREGNATED DISK METHOD FOR TESTING ANTIFUNGAL SUSCEPTIBILITY

BACKGROUND OF THE INVENTION

This invention relates to a method for determining which antifungal agents are effective against a particular fungus and quantifying the concentration at which the antifungal agent is effective.

The susceptibility of fungi to antifungal agents is rarely tested routinely in hospitals, clinics or doctors' offices because of the time consuming procedures, often taking several days, and difficulties related to the stability of the antifungal agents. With present testing methods, it is necessary to make fresh solutions of nutrient or growth media to add to the agar or other non-nutrient support medium which is inoculated with the fungi. This is time consuming, expensive and tedious. Although susceptibility testing with antifungal agents is similar to that with antibacterial agents, there are certain differences which make testing with antifungal compounds more difficult.

Major difficulties include the growth characteristics of fungi in comparison to bacteria and the basic properties of the anti-fungal agents to be tested. Different antifungal agents have different solubilities, reactions to light and heat, etc. Some fungi require specialized types of growth media. In testing the susceptibility of different fungi to various types and concentrations of antifungal agents, generalized mycological growth media may be used, but must be chosen carefully to avoid inactivating the antifungal agent or agents tested.

Two of the main chemotherapeutic agents available in the United States for treatment of serious or systemic mycotic infections in man include amphotericin B and nystatin, both polyenes. The chemical properties of these compounds present problems relating to in vitro susceptibility testing. They are light-sensitive and subject to thermal destruction upon incubation. In addition, they are insoluble in water and unstable in the presence of acid. Therefore, additional precautions in using and testing these antifungal agents are necessary in comparison to many of the common antibacterial agents.

The closest prior art known to applicant is a method of testing antibiotic susceptibility of bacteria by incorporating a growth medium with agar to form nutrient agar in a petri dish. The nutrient agar is inoculated with bacteria and disks impregnated with various antibiotics of different concentration are placed on the inoculated nutrient agar. This method is relatively successful because specific growth media are usually not required for particular bacteria. Such is not the case with fungi, since the choice of growth media may be more dependent on the fungus and antifungal agent being tested.

A faster growth rate of fungi is achieved in the present invention by impregnating the disks with growth medium, rather than mixing the growth medium with the agar as in the prior art. Furthermore, the present invention avoids the necessity of mixing fresh growth medium with the agar each time a test is desired.

U.S. Pat. No. 2,986,497 of Pagano et al. discloses a method for assaying microorganisms comprising inoculating a nutrient and agar mixture contained in a petri dish with the organism to be tested. A sheet of bibulous material having a plurality of spaced apertures is impregnated with a "microorganism-affecting substance" in areas peripheral to at least one aperture. The sheet is then placed on the inoculated nutrient and agar, and the presence and amount of growth is noted. This method has the disadvantage that the nutrient medium must be made up and mixed with the agar at the time it is used. Further, it would be difficult to calculate the quantity of the microorganism-affecting substance present around each aperture of each sheet so that the procedure has limited quantitative value.

U.S. Pat. No. 3,216,907 of Goldman discloses a method for detecting microbial sensitivity to antimicrobial agents. Paper strips impregnated with a special nutrient liquid containing a carefully adjusted trace amount of glucose are required. A antimicrobial agent is applied only to the bottom of the strip or to the bottom of a petri dish. The organism to be tested is placed on top of the strip followed by the addition of one drop of water. After a very brief period of incubation, an inspection is made to determine whether the trace quantity of glucose is present, appreciably diminished or absent. Three control strips are necessary to determine whether the proper trace amount of glucose is present in each of the test strips. If not, the test must be tried again. This has a disadvantage of requiring the precise adjustment of a trace amount of glucose. Another disadvantage is that microorganisms utilize glucose or other metabolite at varying rates, so that an indirect measurement of the amount of glucose utilized is not likely to be very accurate.

U.S. Pat. No. 3,416,998 of Streitfeld discloses the use of transparent disks cut from dried agar sheets and impregnated with any of several testing agents, which may include a drug. Nutrient agar is placed in a petri dish and inoculated with the microorganism used in the test. It is necessary to prepare the nutrient medium to be mixed with the agar shortly prior to the tests. A disk made of the same nutrient agar used in the petri dish and containing the test agent is placed upon the inoculated nutrient agar. Alternatively, the organism may be rubbed on the disk. After an incubation period, the presence or absence of growth is noted. At column 7, lines 40-42, it is stated:

"It is important to note that the agar sheets of the present invention are thin dry brittle sheets incapable of supporting bacterial growth per se."

In the present case, the disks are impregnated with various types of antifungal agents in various concentrations and specific nutrient medium for the particular fungus and antifungal agent being tested. The disks are placed onto non-nutrient agar inoculated with the fungus being tested. Thus, the disks of the present invention are capable of supporting fungal growth per se. In the present invention, the nutrient medium may be stored in a dry condition along with the antifungal agent on the disks.

U.S. Pat. No. 3,509,026 of Sanders discloses a process of testing the sensitivity of bacteria to antibiotics and a test element for use in the process. The test element comprises an inert disk impregnated with a particular antibiotic, nutrient medium and a substrate. The substrate is capable of detecting certain enzymes produced by the bacteria to provide a detectable change which indicates the extent of bacterial growth in the nutrient medium carried by the disk.

The present invention differs from U.S. Pat. No. 3,509,026 in that the present invention is not based on the concept of testing for the production by the organism of a particular enzyme which is detected by a substrate impregnated in the disk. The disks of the present invention contain only an antifungal agent and a nutrient medium for the fungus which is compatible with the antifungal agent being tested. The problems inherent in the process of U.S. Pat. No. 3,509,026 are avoided by the present invention. Those problems include: the non-uniform production of a vital enzyme formed by all bacteria, the different lengths of time it takes different bacteria to form a particular enzyme, and the possible interference of different enzymes or other metabolites formed by the growth of the tested bacteria.

M. Huppert et al., "Rapid Methods For Identification Of Yeasts", *Journal Of Clinical Microbiology*, Vol. 2, No. 1, July, 1975, pp. 21–34, disclose a method for identifying yeasts. The method includes the steps of swabbing the yeast to be identified onto hardened agar in petri dishes, allowing the streaked plates to dry, applying disks impregnated with appropriate growth media, incubating at room temperature and periodically checking the system for color changes. By testing for carbohydrate assimilation, nitrate assimilation, fermentation, urease production, pseudogerm production, production of hyphae or pseudohyphae, etc., the identity of the yeast may be determined. No antifungal agents whatsoever are used in this method.

The preparation of the nutrient media, the antifungal agents and the fungi to be tested in the present invention are similar to those reported in S. Shadomy and A. Espinel-Ingroff, "Susceptibility Testing Of Antifungal Agents", Ch. 63, pp. 569–574 in E. H. Lennett, E. H. Spaulding, and J. P. Truant, Eds., Manual Of Clinical Microbiology, 2nd Ed., American Society for Microbiology, Washington, D.C. (1974). This publication describes the susceptibility testing of antifungal agents, namely, amphotericin B, nystatin and 5-fluoro-cytosine (5-FC), by the "broth dilution method" and the "semi-solid agar dilution method". At pages 570–571, it is stated:

"Diffusion disks are not available in this country for in vitro testing with any of the three agents, although studies are underway to permit application of the diffusion disk method to susceptibility testing with 5-FC."

Thus, this publication teaches away from the use of the disk method of susceptibility testing of antifungal agents according to the present invention.

SUMMARY OF THE INVENTION

The present invention comprises a method for testing the susceptibility of fungi to antifungal agents comprising providing dried disks of inert support material impregnated with nutrient medium capable of sustaining growth of the fungus and at least one antifungal agent to be tested whereby each disk contains a particular known concentration of the antifungal agent, inoculating a non-nutrient medium with the fungus to be tested, placing the dried impregnated disks on the inoculated non-nutrient medium, incubating the disks and the inoculated non-nutrient medium for a time and at a temperature capable of promoting growth of said fungus, and determining the absence or presence and extent of growth of the fungus after the incubation period.

After the initial period of incubation, the minimum inhibitory concentration of the antifungal agent being tested is determined by noting which disks showed no circumscribed growth. Incubation can be continued to determine the minimum fungicidal concentration. Overgrowth of the fungus being tested will occur around those disks containing concentrations of antifungal agent below the minimum fungicidal concentration.

The method of the present invention also may be used to test combinations of antifungal agents. In this method, more than one antifungal agent of known concentration is impregnated in each test disk.

In comparison with prior art methods, the method of the present invention is fast, easy and is of comparable reliability. The disks can be stored for more than two months without becoming unstable. Many determinations of susceptibility can be made after only 24 hours of incubation. These determinations are both qualitative and quantitative.

DETAILED DESCRIPTION OF THE PREFERRED EMBODIMENTS

Before discussing the method of the present invention in detail, the components used in the method will be described. It is to be understood that the described components and methods of preparing them are those which are presently preferred. They should not be construed as the only components and methods which may be used in accordance with the present invention.

The present invention is a method for testing the susceptibility of fungi to antifungal agents. "Fungi" is to be interpreted broadly as including all types of fungi, including yeasts and filamentous fungi. The presently preferred method of preparing the fungus to be tested is by using a culture grown for about 24 to about 48 hours in yeast nitrogen base containing 1% glucose and 0.15% asparagine commercially available from Difco Laboratories. The cultures are centrifuged, the supernatant is removed, the remaining sedimented cells are washed with sterile distilled water, and sterile distilled water is added to the sedimented cells until a cloudy suspension results. For particular uniformity in testing, it may be desirable to adjust the cell concentration to 80% transmission at about 520 nm using a spectrophotometer or to use the standard "Wickersham card technique".

The non-nutrient medium to be innoculated with the fungus may be sterile liquified 2% purified agar, such as is commercially available from Difco Laboratories, placed in a petri dish and allowed to harden into a confluent surface. Any other suitable non-nutrient medium known in the art may also be used. The surface of the non-nutrient medium is inoculated by swabbing, streaking or any other suitable method of uniform inoculation. The uniformly inoculated non-nutrient medium is then allowed to dry.

The disks used in the present invention may be made of blotting paper, filter paper or any other suitable inert, liquid-absorbent material. Filter paper is presently preferred. The disks can be in any shape and any convenient size. Different shapes of disks may be selected to indicate different types or concentrations of antifungal agents being tested. The disks may contain other indicia, such as printing, embossing, etc.

Each disk is impregnated with a particular known concentration of at least one particular antifungal agent, except for the control disks. When the susceptibility of a fungus to combinations of antifungal agents is being tested, more than one antifungal agent is impregnated in each test disk.

The disks are also impregnated with a suitable nutrient medium capable of sustaining growth of the fungus being tested. One suitable nutrient medium is an aqueous solution comprising about 6.5 grams per liter (g/l) yeast extract, about 1.5 g/l beef extract, about 5 g/l peptone, about 10 g/l pancreatic digest of casein, about 11 g/l dextrose, about 3.5 g/l sodium chloride, about 3.68 g/l dipotassium phosphate and about 1.32 g/l monopotassium phosphate or equivalent amounts thereof. The solution is autoclaved and allowed to cool. The solution has a final pH of 6.6. Yeast nitrogen base is another suitable nutrient medium for use in the present invention. Nutrient broth, commercially available from Difco Laboratories, may also be used with certain fungi.

Stock solutions of the antifungal agents to be tested are preferably prepared by diluting the antifungal agents in the proper nutrient medium. It is presently preferred to prepare dilutions in 10 ml of the proper medium to give the following final concentrations when applied to the disks (all quantities in micrograms per milliliter): 0.05, 0.08, 0.09, 0.1; 0.1 increment increases to 0.9, 1.0; 0.5 increment increases to 10.0; and 12.0, 14.0, 20.0, 25.0 and 50.0. Disks have been prepared by placing 0.05 ml of the above dilutions of antifungal agent containing medium on 6.5 mm diameter disks in 0.01 or 0.02 ml increments. The impregnated disks are then allowed to dry at a temperature preferably below about 10° C. Disks dried at 4° C. have been found to be suitable. The disks may also be dried by a lyophilization or freeze drying process.

Antifungal agents which have been successfully employed in the present method include amphotericin B and nystatin. Because these antifungal agents are polyenes, it is preferable to prepare solutions of amphotericin B and nystatin by solubilizing them with dimethyl sulfoxide, deoxycholate or other suitable solvent prior to diluting them with the nutrient medium.

5-fluorocytosine is another antifungal agent which has been successfully tested in accordance with the present invention. Stock solutions of 5-fluorocytosine were prepared by diluting the antifungal agent in yeast nitrogen base. Control disks are prepared by impregnating the disks with nutrient medium used in the test disks. Thus, if amphotericin B or nystatin were being tested, then the control disks should also contain dimethyl sulfoxide, deoxycholate or other suitable solvent.

Dried disks which have been stored for more than two months at −10° C. in a nitrogen atmosphere have remained active. This storage ability with comparable stability is lacking in the prior art. Because the disks used in the present invention may be stored for extended periods of time, it is not necessary to make up solutions of nutrient medium at the time of or immediately before a susceptibility test is performed. This allows for easier and more standardized testing of the susceptibility of fungi to antifungal agents.

To perform the tests in accordance with the present inventions, disks impregnated with various concentrations of antifungal agent and nutrient medium and a control disk impregnated only with the corresponding nutrient medium are placed on the fungus to be tested which has been applied to the non-nutrient medium. The disks are the inoculated non-nutrient medium are then incubated at a suitable temperature for a sufficient time to promote growth of the fungus. Any temperature is suitable if it will promote growth of the fungus without adversely affecting the fungus or the activity of the antifungal agent or agents tested. The time of incubation can be determined by observing the extent of growth around the control disk. Incubation at temperatures of about 28° C. to about 31° C. for about 24 to about 48 hours has been found to be suitable. Incubation at 29° C. for about 24 hours has been found to be suitable, except for some types of filamentous fungi which should be incubated for 48 hours. The zones of growth or inhibition around the disks were read at 6, 12, 24, 36 and 48 hours after the disks were placed on the tested fungus.

The minimum inhibitory concentration is defined as the lowest concentration of antifungal agent which inhibits visible growth. The disks containing concentrations of antifungal agents below the minimum inhibitory concentration show circumscribed growth of the fungus around the disk. Disks containing concentrations of antifungal agent at or above the minimum inhibitory concentration show no circumscribed growth.

Minimum fungicidal concentration is defined as the lowest concentration of antifungal agent from which subcultures were negative or where no overgrowth occurs. In tests of *Candida albicans,* the minimum inhibitory concentration can usually be determined at about 24 hours. Minimum fungicidal concentration may be determined by incubation for an additional 24 hours. At concentrations below the minimum fungicidal concentration, overgrowth occurs by 48 hours.

The invention will now be described in more detail with reference to the following specific, non-limiting examples:

EXAMPLE 1

Clinical isolates of various fungi listed in Table 1 were obtained from different patients diagnosed as having fungal infections. The fungal inocula were prepared by using a 24–48 hour cultures grown in yeast nitrogen base containing 1% glucose and 0.15% asparagine. After centrifuging, the supernatant was removed, the sedimented cells were washed twice with sterile distilled water and a cell suspension was adjusted to 80% transmission at 520 nm using a Beckman DB-GT grating spectrophotometer.

Sterile liquified 2% purified agar was placed in petri dishes and allowed to harden. The surface of the agar was inoculated with a sterile cotton swab saturated with a suspension of an organism. The uniformly swabbed plates were then allowed to dry.

Disks were prepared using the dilutions described above for amphotericin B, nystatin and 5-fluorocytosine. 0.05 ml of the dilutions of each antifungal agent diluted with the appropriate nutrient medium were pipetted on 6.5 mm diameter disks. The disks were dried at 4° C. after each application. Control disks were also prepared.

Several test disks and a control disk were placed in each petri dish containing the inoculated agar. The disks and petri dishes were then incubated at 29° C. and the minimum inhibitory concentration of the various concentrations of the antifungal agents were read at 6, 12, 24, 36 and 48 hours.

The organisms tested gave the results set forth in Table 1 and were found to be comparable to those obtained by the broth dilution method when read at 24 or 48 hours. In 10 duplicate runs with each strain tested, the variation in minimum inhibitory concentration averaged ±0.05 μg/ml.

The minimal fungicidal concentrations of amphotericin B for the first 6 isolates of *Candida albicans* listed in Table 1 were determined by incubating the disks and organisms for 48 hours. At concentrations below the minimum fungicidal concentration, overgrowth occurred by 48 hours. As shown in Table 2, the results of the determination of minimum fungicidal concentrations compared favorably with the determination by the standard broth dilution method of Shadomy et al.

Table 1

Comparison of minimum inhibitory concentrations of three antifungal agents against clinically isolated strains of fungi tested by disk and broth dilution methods*

| Organism | Minimum Inhibitory Concentration ($\mu$g/ml) | | | | | |
|---|---|---|---|---|---|---|
| | Amphotericin B | | Nystatin | | 5-Fluorocytosine | |
| | Disk | Broth | Disk | Broth | Disk | Broth |
| Candida albicans (isolate 1) | 0.30 | 0.40 | 1.50 | 1.50 | 8.50 | 6.50 |
| C. albicans (isolate 2) | 0.60 | 0.70 | 4.50 | 5.00 | 0.30 | 0.60 |
| C. albicans (isolate 3) | 0.08 | 0.10 | 1.50 | 1.50 | 2.00 | 3.00 |
| C. albicans (isolate 4) | 0.60 | 0.60 | 3.50 | 3.50 | 6.00 | 3.50 |
| C. albicans (isolate 5) | 0.90 | 0.80 | 4.00 | 4.00 | 0.80 | 0.70 |
| C. albicans (isolate 6) | 1.00 | 1.50 | 6.50 | 6.00 | 0.50 | 0.70 |
| C. albicans (isolate 7) | — | — | 0.30 | 0.20 | — | — |
| C. parapsilosis (isolate 1) | 0.50 | 0.80 | 3.50 | 4.50 | 0.90 | 0.80 |
| C. parapsilosis (isolate 2) | 0.60 | 0.60 | 4.50 | 5.00 | 1.50 | 2.00 |
| C. tropicalis | 0.70 | 0.80 | 5.50 | 6.00 | 7.50 | 6.00 |
| Cryptococcus neoformans (isolate 1) | 0.40 | 0.50 | 2.00 | 2.50 | 10.00 | 8.50 |
| C. neoformans (isolate 2) | 0.20 | 0.40 | 3.00 | 3.00 | 15.00 | 12.00 |
| C. neoformans (isolate 3) | 0.50 | 0.50 | — | — | — | — |
| Geotrichum candidum | 0.80 | 0.90 | 5.00 | 4.50 | 2.50 | 3.00 |
| Saccharomyces cerevisiae (isolate 1) | 0.40 | 0.40 | 2.00 | 2.50 | 1.50 | 2.50 |
| S. cerevisiae (isolate 2) | 0.60 | 0.80 | 1.00 | 2.00 | 0.80 | 1.00 |
| Trichosporon sp. | 0.90 | 1.10 | 3.50 | 3.00 | 50.00 | 50.00 |
| Torulopsis glabrata | 0.20 | 0.30 | 3.00 | 4.50 | 0.80 | 0.70 |

*Broth dilution method conducted in accordance with S. Shadomy and E. Espinel-Ingroff, "susceptibility Testing of Antifungal Agents", Ch. 63, pp. 569-574 in E. H. Spaulding and J. P. Truant, Eds., Manual Of Clinical Microbiology, 2nd Ed., American Society for Microbiology, Washington, D.C. (1974)

Table 2

Comparison of minimum fungicidal concentrations of amphotericin B for clincially isolated strains of Candida albicans tested by disk and broth dilution methods

| Isolate | Minimum Fungicidal Concentrations ($\mu$g/ml) | |
|---|---|---|
| | Disk | Broth |
| 1 | 1.40 | 1.50 |
| 2 | 1.60 | 1.60 |
| 3 | 0.90 | 0.80 |
| 4 | 0.90 | 1.10 |
| 5 | 1.80 | 1.60 |
| 6 | 5.00 | 6.50 |

The susceptibility of two other isolates to combinations of antifungal agents were tested by combining more than one antifungal agent on each test disk. A series of test disks were prepared containing various combinations of antifungal agents in various concentrations and were used in the method of the present invention. The results of this procedure are summarized in the following specific, non-limiting examples:

EXAMPLE 2

For a Candida albicans isolate previously tested for amphotericin B susceptibility at 0.8 $\mu$g/ml, a combination of amphotericin B and tetracycline tested according to the present invention resulted in amphotericin B susceptibility of 0.2 $\mu$g/ml and tetracycline susceptibility of 0.1 $\mu$g/ml. This is a significant reduction in amphotericin B.

EXAMPLE 3

An isolate of Candida tropicalis was initially tested for amphotericin B susceptibility of 0.5 $\mu$g/ml. When a combination of amphotericin B and tetracycline were combined on the disks used in the testing procedure according to the present invention, effective inhibition of the isolate occurred using 0.05 $\mu$g/ml of amphotericin B and 0.2 $\mu$g/ml of tetracycline.

These latter examples demonstrate that the method of the present invention can be used for testing the susceptibility of fungi to a combination of antifungal agents.

The word "solution" as used herein is meant to include not only true solutions, but also suspensions, emulsions and dispersions.

The present invention may be embodied in other specific forms without departing from the spirit or essential attributes thereof and, accordingly, reference should be made to the appended claims, rather than to the foregoing specification as indicating the scope of the invention.

I claim:

1. A method for testing the susceptibility of a fungus to antifungal agents comprising providing dried disks consisting essentially of inert support material impregnated with nutrient medium which is capable of sustaining growth of said fungus and which does not inactivate or antifungal agent to be tested and at least one antifungal agent to be tested whereby each disk contains a particular known concentration of said antifungal agent, inoculating a non-nutrient support medium with the fungus to be tested, placing said dried impregnated disks on said inoculated non-nutrient support medium, incubating said disks and said inoculated non-nutrient support medium for a time and at a temperature capable of promoting growth of said fungus, and determining the absence or presence and extent of growth of said fungus after said incubation period.

2. A method according to claim 1 wherein said fungus to be inoculated on said non-nutrient medium is prepared by using a culture grown for about 24 to about 48 hours in yeast nitrogen base containing about 1% glucose and about 0.15% asparagine, centrifuging said culture, removing the supernatant, washing the remaining sedimented cells and adding sterile distilled water until a cloudy suspension results.

3. A method according to claim 1 wherein said non-nutrient support medium is sterile liquified 2% purified agar which has been allowed to harden.

4. A method according to claim 1 wherein said antifungal agent is selected from the group consisting of amphotericin B and nystatin.

5. A method according to claim 1 wherein said antifungal agent is 5-fluorocytosine.

6. A method according to claim 1 wherein said antifungal agent is diluted with said nutrient medium.

7. A method according to claim 1 wherein said nutrient medium comprises an aqueous solution comprising about 6.5 g/l yeast extract, about 1.5 g/l beef extract, about 5 g/l peptone, about 10 g/l pancreatic digest of casein, about 11 g/l of dextrose, about 3.5 g/l of sodium chloride, about 3.68 g/l of dipotassium phosphate and about 1.32 g/l of monopotassium phosphate or equivalent amounts thereof.

8. A method according to claim 1 including placing control disks impregnated with nutrient medium on said inoculated non-nutrient support medium.

9. A method according to claim 1 wherein said disks are dried at or below about 10° C.

10. A method according to claim 9 wherein said disks are dried by a lyophilization process.

11. A method according to claim 1 wherein said disks and inoculated non-nutrient support medium are incubated for about 24 to about 48 hours at a temperature of about 28° C. to about 31° C.

12. A method according to claim 11 wherein said disks and inoculated non-nutrient support medium are incubated at about 29° C. for 24 hours to determine the minimum inhibitory concentration of the tested antifungal agent.

13. A method according to claim 1 wherein said disks and said inoculated non-nutrient support medium are incubated for about 48 hours to determine the minimum fungicidal concentration of said antifungal agent.

14. A method according to claim 1 wherein said disks are impregnated with combinations of antifungal agents.

15. A disk-agar method for testing the susceptibility of a fungus to antifungal agent comprising impregnating disks consisting essentially of inert support material with nutrient medium which is capable of sustaining growth of said fungus and which does not inactivate an antifungal agent to be tested and at least one antifungal agent to be tested, whereby each disk contains a particular known concentration of said antifungal agent, drying said impregnated disks at a temperature at or below about 10° C., inoculating a non-nutrient agar with the fungus to be tested, placing said dried impregnated disks on said inoculated non-nutrient agar, incubating said disks and said inoculated non-nutrient agar for a time and at a temperature capable of promoting growth of said fungus, and determining the absence or presence and extent of growth of said fungus after said incubation period.

* * * * *